United States Patent
Storm, Jr. et al.

(10) Patent No.: US 6,688,176 B2
(45) Date of Patent: Feb. 10, 2004

(54) SINGLE TUBE DENSITOMETER

(75) Inventors: Bruce H. Storm, Jr., Houston, TX (US); James Masino, Houston, TX (US); Mark A. Proett, Missouri City, TX (US); Michael T. Pelletier, Houston, TX (US)

(73) Assignee: Halliburton Energy Services, Inc., Dallas, TX (US)

( * ) Notice: Subject to any disclaimer, the term of this patent is extended or adjusted under 35 U.S.C. 154(b) by 38 days.

(21) Appl. No.: 10/055,202

(22) Filed: Oct. 29, 2001

(65) Prior Publication Data

US 2002/0184940 A1 Dec. 12, 2002

Related U.S. Application Data

(63) Continuation-in-part of application No. 09/482,793, filed on Jan. 13, 2000, now Pat. No. 6,378,364.

(51) Int. Cl.$^7$ ............................. E21B 44/00; G01F 1/84
(52) U.S. Cl. ................. 73/579; 73/152.47; 73/861.355; 73/32 A
(58) Field of Search ............................. 73/579, 152.47, 73/861.355, 861.356, 861.357, 24.06, 23.28, 32 A

(56) References Cited

U.S. PATENT DOCUMENTS

| | | | |
|---|---|---|---|
| 3,688,188 A | * 8/1972 | Bak et al. ................. 324/636 |
| 3,831,433 A | * 8/1974 | Kovacs et al. ............... 73/32 A |
| 4,255,964 A | * 3/1981 | Morison .................... 73/24.01 |
| 4,823,614 A | 4/1989 | Dahlin, Erik B. ......... 73/861.38 |
| 5,005,400 A | 4/1991 | Lew ............................... 73/32 |
| 5,009,109 A | 4/1991 | Kalotay et al. ........... 73/861.38 |
| 5,048,349 A | 9/1991 | Wolff ...................... 73/861.37 |
| 5,363,706 A | 11/1994 | Lew ......................... 73/861.38 |
| 5,383,349 A | * 1/1995 | Blake-Coleman ........... 73/32 A |
| 5,533,381 A | * 7/1996 | Seale ......................... 73/19.03 |
| 5,796,012 A | 8/1998 | Gomi et al. ............ 73/861.357 |
| 5,827,979 A | 10/1998 | Schott et al. ........... 73/861.357 |
| 6,378,364 B1 | * 4/2002 | Pelletier et al. ........... 73/152.47 |
| 6,543,281 B2 | * 4/2003 | Pelletier et al. ........... 73/152.47 |

FOREIGN PATENT DOCUMENTS

AU 551888 5/1986

OTHER PUBLICATIONS

*Measurement & Control News*, Sep. 1993, vol. 27, No. 4 Issue 160 12 pp.
*Mass Flowmeters*, Flow Measurement, Copyright © Instrument Society of America 1991, pp. 221–247.
*Straight–Tube Mass Flow and Density Meters*, Micro Motion T–Series, Product Data Sheet, PS–00371, Jun. 1999, 8 pp.

* cited by examiner

*Primary Examiner*—Hezron Williams
*Assistant Examiner*—Rose M. Miller
(74) *Attorney, Agent, or Firm*—Michael W. Piper

(57) ABSTRACT

A measurement device is provided that determines fluid properties from vibration frequencies of a sample cavity. In one embodiment, the measurement device includes a sample flow tube, vibration source and detector mounted on the tube, and a measurement module. The sample flow tube receives a flow of sample fluid for characterization. The measurement module employs the vibration sources to generate vibrations in the tube. The measurement module combines the signals from the vibration detector on the tube to determine properties of the sample fluid, such as density, viscosity, compressibility, water fraction, and bubble size. The measurement module may further detect certain flow patterns such as slug flow, for example. To measure the sample fluid density, the measurement module determines the resonant frequency of the sample flow tube. The density can then be calculated according to a formula that compensates for the temperature and pressure of the system.

7 Claims, 5 Drawing Sheets

SINGLE TUBE DENSITOMETER

CROSS-REFERENCE TO RELATED APPLICATIONS

This is a continuation-in-part application of U.S. patent application Ser. No. 09/482,793, filed Jan. 13, 2000 now U.S. Pat. No. 6,378,364 and entitled "Downhole Densitometer," which is hereby incorporated herein by reference.

BACKGROUND OF THE INVENTION

The present invention relates generally to devices and methods for measuring fluid density and other fluid flow properties in a flow stream, where fluid is taken to mean any liquid, gas, or mixture thereof, including those which contain solids. More particularly, the present invention relates to a high-accuracy density and viscosity measurement device suitable for use in a high-temperature, high-pressure, high-shock environment such as may be encountered in a wellbore.

There are many instances in industrial processes and controls for handling flowing fluids where the density of the moving fluid has to be determined accurately. One particular application is in the identification of reservoir fluids flowing in a well. Water often co-exists with gaseous hydrocarbons and crude oil in some common geologic formations. As such, a mixture of water, gaseous hydrocarbons, and liquid hydrocarbons is often produced by a working oil well, and the mixture is ultimately separated at a downstream location. It is often desirable to determine the amount of oil that is produced in a stream flowing from a formation. To accurately determine the amount of crude oil extracted from a formation, a "net oil computer" may be used to ascertain the amount of crude oil. The "net oil computer" determines the total volume flow rate of the flow stream and calculates the flow stream's oil percentage (based on density measurements) to determine the net amount of oil that emanates from the formation. Given the large quantities of crude oil that are usually involved, any small inaccuracies in measuring density can disadvantageously accumulate over a relatively short interval of time to become a large error in a totalized volumetric measure.

Another particular application of density measurement is to determine the mass flow rate of a fluid medium. Mass flow rate can be calculated as a product of a fluid density (determined by a densitometer) and a volume flow rate of the fluid (measured by a volumetric flowmeter). There are mass flowmeters available at the present time, including such types as Coriolis mass flowmeters and thermal-probe mass flowmeters. These types of mass flowmeters, while they function excellently in the mass flow measurement of low viscosity fluids, work poorly in measuring flows of highly viscous fluids because the fluid's viscosity introduces error in the data acquisition for the mass flow rate. One of the more promising approaches to measurement of the mass flow rate is to combine an accurate densitometer and a reliable volumetric flowmeter. This combination is particularly effective in measuring mass flow rates of highly viscous fluids or mixtures of fluids and gasses.

Coriolis mass flowmeters are one type of flowmeter that can be used to measure the density of an unknown process fluid. As taught, for example, in U.S. Pat. No. 4,491,025, issued to Smith et al., a Coriolis meter may contain two parallel conduits, each typically being a U-shaped flow tube. Each flow tube is driven such that it oscillates about an axis. As the process fluid flows through each oscillating flow tube, movement of the fluid produces reactionary Coriolis forces that are perpendicularly oriented to the plane of the fluid's angular velocity in the tube. These reactionary Coriolis forces cause each tube to twist about a torsional axis that, for U-shaped flow tubes, is normal to its bending axis. The net effect is a slight deformation and deflection of the conduit proportional to the mass flow rate of the fluid. This deformation is normally measured as a small difference between the deflection at the inlet ends of the conduits compared to the deflection at the outlet ends. Both tubes are oppositely driven such that each tube behaves as a separate tine of a tuning fork and thereby cancels any undesirable vibrations that might otherwise mask the Coriolis forces.

The resonant frequency at which each flow tube oscillates depends upon its total mass, i.e. the mass of the empty tube itself plus the mass of the fluid flowing therethrough. Inasmuch as the total mass will vary as the density of the fluid flowing through the tube varies, the resonant frequency will likewise vary with any changes in density.

As specifically taught in U.S. Pat. No. 4,491,009, issued to Reusch, the density of an unknown fluid flowing through an oscillating flow tube is proportional to the square of the period at which the tube resonates. While the circuit taught in Reusch may provide accurate density measurements, it unfortunately possesses several drawbacks. First, for certain applications, density measurements to an accuracy of one part in 10,000 are necessary. An accuracy of this magnitude is generally not available through an analog circuit unless highly precise analog components are used. Such components are quite expensive. Second, the analog circuit disclosed in this patent cannot be independently calibrated to compensate for changing characteristics of the electronic components—such as offset, drift, aging and the like. Specifically, this circuit is calibrated on a "lumped" basis, i.e. by first passing a known fluid, such as water, through the meter and then adjusting the circuit to provide the proper density reading at its output. This process compensates for any errors that occur at the time of calibration that are attributable either to physical errors in measuring density using a Coriolis mass flow meter or to errors generated by the changing characteristics of the electrical components themselves. Unfortunately, after the circuit has been calibrated in this fashion, component characteristics will subsequently change over time and thereby inject errors into the density readings produced by the circuit. This, in turn, will eventually necessitate an entire re-calibration.

An exemplary densitometer is disclosed in patent application Ser. No. 09/482,973, by Pelletier et al. The above referenced application discloses a measurement device for determining fluid properties from vibration frequencies of a sample cavity and a reference cavity. In one embodiment, the measurement device includes a sample flow tube, a reference flow tube, vibration sources and detectors mounted on the tubes, and a measurement module. The sample flow tube receives a flow of sample fluid for characterization. The reference flow tube is filled with a reference fluid having well-characterized properties. The reference flow tube may be pressure balanced to the same pressure as the sample. The measurement module employs the vibration sources to generate vibrations in both tubes. The measurement module combines the signals from the vibration detectors on the tubes to determine properties of the sample fluid, such as density, viscosity, compressibility, water fraction, and bubble size. The measurement module may further detect certain flow patterns such as slug flow, for example.

To determine the sample fluid density, the measurement module measures the difference between resonance frequencies of the sample flow tube and the reference flow tube. The density can then be calculated according to a formula. Other fluid properties may be determined from the sample tube's resonance peak amplitude, peak width and/or peak shape. Variation of the density measurements may be used to detect and characterize multiple phase fluid flow. The use of a reference tube in the disclosed measurement device greatly enhances the accuracy and reliability of the measurement device over a range of temperatures, pressures, and shock accelerations such as those that may be found in a borehole.

Most of the densitometers described above use very sensitive electrical receivers to convert the vibration of the flow tube into an electrical signal that can then be processed into useful information. The need for increasing accuracy in downhole flow evaluation has led to the development of receivers of increasing sensitivity. Because of the limited envelope available in downhole applications, the transmitter is often located in close proximity to the receiver. This close proximity between the transmitter and receiver is thought to cause interference between the two components, which is likely a result of the interaction between the magnetic fields of the components. This is of particular concern with the receiver because any interference may distort the signal and cause difficulty in accurately recognizing the vibratory response of the flow tube. In order to minimize the effects of this problem, many of the prior art methods have used multiple flow tubes to create a reference point to cancel out external interference.

It may be appreciated from the foregoing that a need exists in the art for a high-accuracy densitometer which is capable of operation under the high temperature, pressure, shock and vibration conditions encountered in a wellbore; which uses relatively inexpensive components; which substantially eliminates any error caused by changing characteristics of any of the electronic components; and which effectively eliminates the errors associated with the effects of temperature and pressure on the system.

SUMMARY OF THE INVENTION

Accordingly, there is disclosed herein a measurement device for determining fluid properties from vibration amplitudes of a sample cavity. In one embodiment, the measurement device includes a sample flow tube, a vibration source, a vibration detector, and a measurement module. The vibration source and vibration detector are arranged in such a manner to minimize any interference in the measured signal. The sample flow tube receives a flow of sample fluid for characterization. The measurement module employs the vibration source to generate vibrations in the tube. The measurement module analyzes the measured signal from the vibration detector on the tube to determine properties of the sample fluid, such as density, viscosity, compressibility, water fraction, and bubble size. The measurement module may further detect certain flow patterns such as slug flow, for example.

To determine the sample fluid density, the measurement module identifies the resonance frequency of the sample flow tube. The density can then be calculated according to a formula that compensates for the temperature and pressure response of the system. The measurement device has preferably calibrated so that the device can compensate for varying temperature and pressure in the wellbore. Other fluid properties may also be determined from the sample tube's resonance peak amplitude, peak width and/or peak shape. Variation of the density measurements may be used to detect and characterize multiple phase fluid flow. The use of the present invention is expected to greatly enhance the accuracy and reliability of the measurement device over a range of temperatures, pressures, and shock accelerations such as those that may be found in a borehole.

BRIEF DESCRIPTION OF THE DRAWINGS

A better understanding of the present invention can be obtained when the following detailed description of the preferred embodiment is considered in conjunction with the following drawings, in which.

Figure 1:
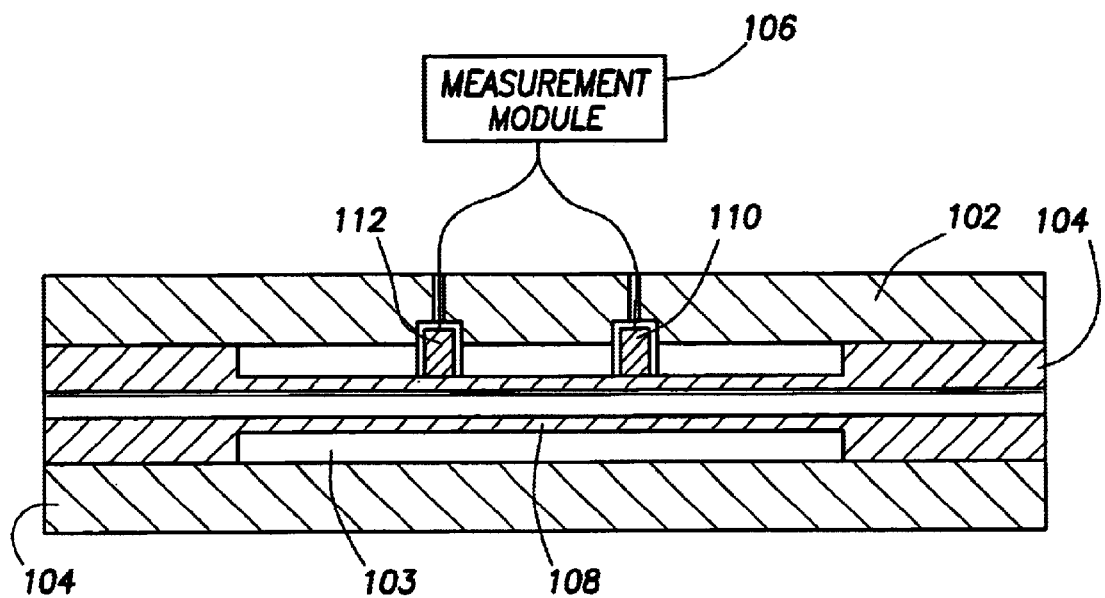
FIG. 1 shows one embodiment of a densitometer according to the present invention.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENT

Apparatus/Tube/Sensors

Referring now to FIG. 1, one embodiment of a device for measuring density and viscosity of a flowing fluid generally includes a rigid housing 102, two bulkheads 104, a single flow tube 108, a single vibration source 110, a single vibration detector 112, and a measurement module 106. The rigid housing 102 surrounds and protects a volume 103 through which the flow tube 108 passes and reduces the response to vibrations not associated with particular vibratory modes of the flow tube 108. The bulkheads 104 seal the volume and secure the flow tube 108 within that volume. The volume 103 preferably contains air, a vacuum or a relatively inert gas such as nitrogen or argon. If gasses are used, then they are preferably at atmospheric pressure when the device is at room temperature.

The rigid housing 102, bulkheads 104, and flow tube 108 are preferably made from material in a configuration that can withstand pressures of more than 20,000 psi (pounds per square inch) at temperatures of 250° C. or more. Two examples of suitable materials are Titanium and Hastaloy-HA276C. Preferably, the bulkheads 104 and the flow tube 108 are constructed from the same piece of material, with the bulkheads 104 being regions of larger diameter on either end of the tube 108. Alternatively, the flow tube 108 may be welded to the bulkheads 104, or otherwise attached. The flow tube 108 may also be secured to the rigid housing 102 by o-rings or other types of elastomeric means. Preferably, the rigid housing 102, bulkheads 104, and the flow tube 108 are constructed from the same material in order to alleviate thermally induced stresses when the system is in thermal equilibrium.

The flow tube 108 is preferably straight, as this reduces any tendencies for plugging and erosion by materials passing through the flow tube 108. However, it is recognized that bent tubes of various shapes, including "U"-shaped tubes, may provide greater measurement sensitivities. Contemplated dimensions for the embodiment of FIG. 1 are shown in Table 1:

TABLE 1

|  | Flow Tube | Bulkhead | Housing |
| --- | --- | --- | --- |
| Length | 6" | 2" | 10" |
| Outer Diam | 0.304" | 1.5" | 2" |
| Inner Diam | 0.219" | — | ~1.5" |

However, it is noted that other dimensions may be used without departing from the scope of the invention.

Figure 2:
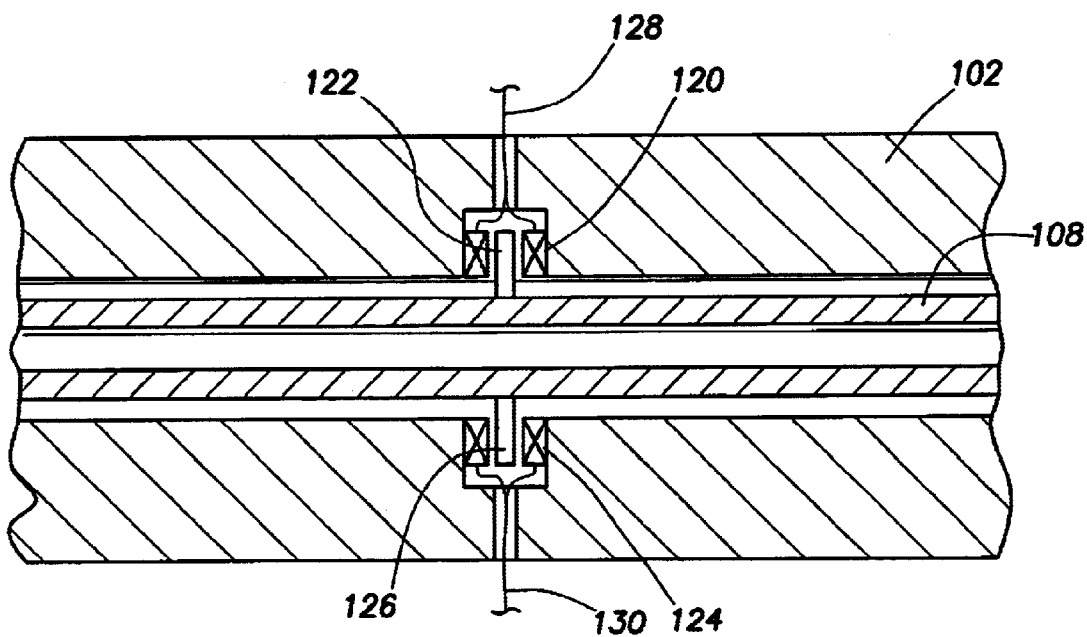
FIG. 2 shows another embodiment of a densitometer according to the present invention.
Figure 3A:
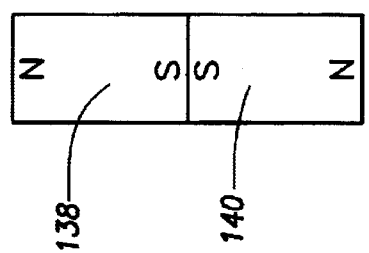
FIG. 3A is an electrical schematic depicting one embodiment of the receiver arrangement in accordance with the present invention.
Figure 3:
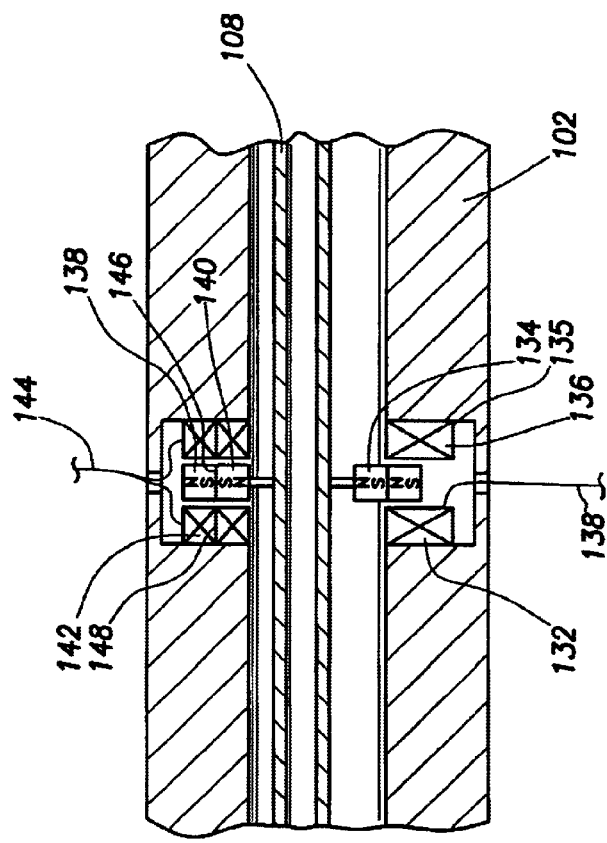
FIG. 3 shows one embodiment of the receiver and transmitter arrangements in accordance with the present invention.

As described above, attached to the flow tube 108 are a vibration source 110 and a vibration detector 112. The vibration source 110 and vibration detector 112 may be located side by side as shown in FIG. 1 or, alternatively located on opposite sides of the flow tube 108 at a point half way between the bulkheads 104, as shown in FIGS. 2 and 3. Other source/detector configurations are also contemplated.

Now referring to FIG. 2, one embodiment of the present invention is illustrated comprising a flow tube 108, two toroidal coils 120, 124 connected to the housing 102, and two ferrous rods 122, 126 connected to the flow tube 108. The coils 120, 124 may also incorporate a ferrous core to form a more effective electromagnet. One coil 120 is connected by electrical leads 128 to a transmitter (not shown). Application of an alternating current to the coil 120 exerts an electromagnetic force on the rod 122, which causes the rod 122 to translate linearly, therefore imparting a vibration on the tube 108. The other coil 124 is connected by leads 130 to a receiver (not shown). The vibration in the tube 108 moves the rod 126 within the coil 124, therefore creating a voltage to generate at the leads 130 that is monitored by the receiver.

The above described configuration has the advantage of using the lightest weight ferrous rod 122, 126 and yields higher sensitivity to density changes than similar applications with heavier rods. The disadvantages are that more power is required to drive the tube and the receiver is not as effective as desired. As discussed above, the effectiveness of the receiver may be limited by interference created by the interaction of the magnetic fields of the transmitter and receiver.

Now referring to FIG. 3, a more effective vibration source 132 is illustrated, comprising a magnet 134 secured to the flow tube 108, and a single coil winding 136 secured to the housing 102. The coil 136 is connected by leads 138 to a transmitter (not shown). The coil 136 is mounted toward the outer extreme of the magnet 134 (this is exaggerated in the figure for clarity). The precise mounting location of the coil 136 is empirically determined by maximizing the vibration force imparted upon the flow tube 108 Applying an alternating current to the coil 136 causes a resulting electromagnetic force that vibrates the flow tube 108.

Still in reference to FIG. 3, the preferred embodiment of the vibration detector is illustrated comprising two magnets 138, 140 secured to the vibrating flow tube 108, and a dual coil winding 142 secured to the housing 102. The dual coil 142 is connected by leads 144 to a receiver (not shown). The symmetry axes of the magnets 138, 140 and dual coil 142 are aligned and the magnets 138, 140 are arranged such that their magnetic fields repel. The dual coil 142 is preferably composed of two identical coils mounted end-to-end with symmetry axes aligned and electrically connected in series. A schematic of the dual coil 142 is presented in FIG. 3A. The plane 146 defined by the interface of the magnets 138, 140 is aligned with plane 148 defined by the intersection of the opposing coil windings of the dual coil 142 as shown in FIG. 3. The coils are connected so as to be phased in such a way that minimal or no voltage is generated at the leads 144 if the coils are placed in a uniform magnetic field (such as that induced by current flow in the nearby vibration source). However, the coils do respond to movement of the opposed magnet pair. Applying a vibration to the flow tube 108 causes a voltage to generate at the leads 144 of the dual coil 142.

The unique arrangement of the vibration detector magnets 138, 140 acts to minimize the magnetic field created by the vibration detector as well as the effects of the magnetic field created by the vibration source. The net effect of this arrangement is to decrease the interference created in the signal produced by the vibration detector, which allows variations in the vibration of the flow tube 108 to be more accurately and reliably detected.

It is noted that in both embodiments, the vibration sources and vibration detectors are preferably mounted near an antinode (point of maximum displacement from the equilibrium position) of the mode of vibration they are intended to excite and monitor. It is contemplated that more than one mode of vibration may be employed (e.g. the vibration source may switch between multiple frequencies to obtain information from higher resonance harmonic frequencies). The vibration sources and detectors are preferably positioned so as to be near antinodes for each of the vibration modes of interest.

The locations of nodes (points of zero vibrational amplitude) and antinodes are determined by the wavelength of the vibration mode and by the mounting of the tube 108. The frequency $f$ and wavelength $\lambda$ are related to the speed of sound $v$ in the material by the equation $$v = f\lambda.$$

Measurement Module

Figure 4:
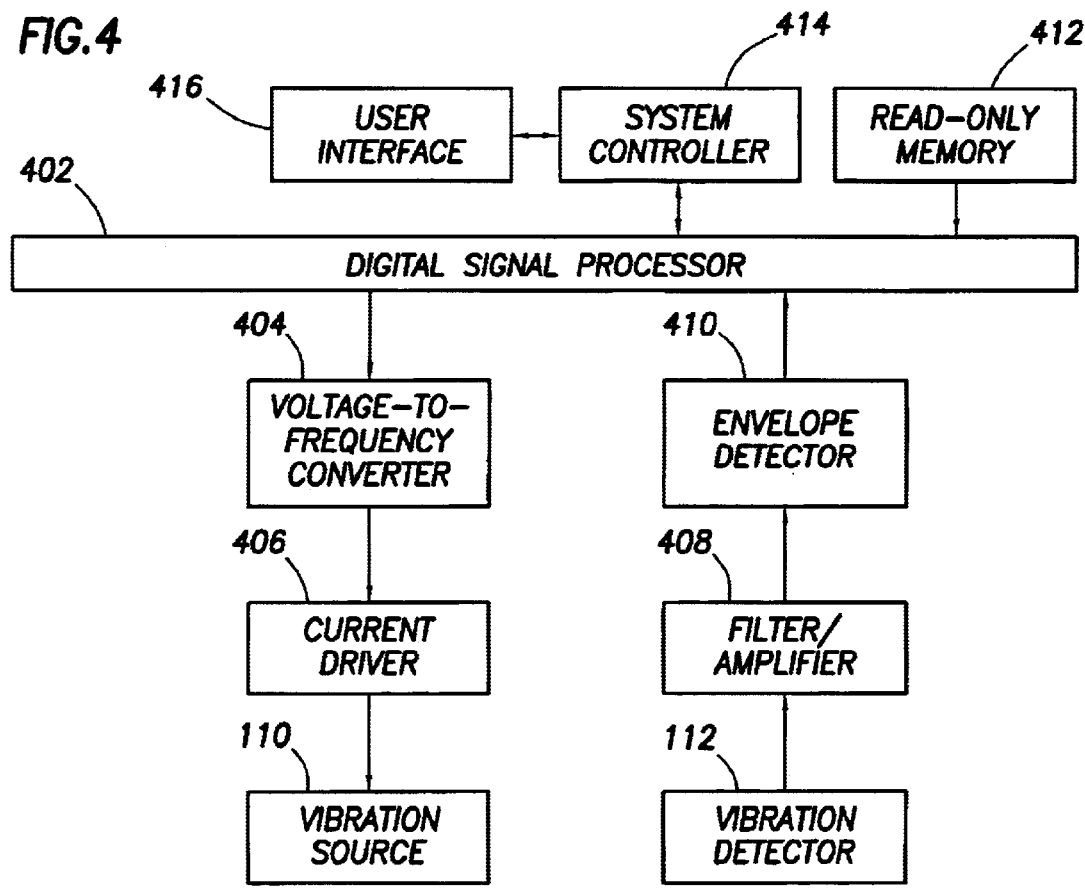
FIG. 4 shows an exemplary measurement module.

Referring now to FIG. 4, one embodiment of the measurement module generally includes a digital signal processor 402, voltage-to-frequency converter 404, current driver 406, filter/amplifier 408, amplitude detector 410, and a read-only memory (ROM) 412. The digital signal processor 402 may be configured and controlled by a system controller 414 that operates in response to actions of the user on the user interface 416. The system controller 414 preferably also retrieves measurements from the digital signal processor 402 and provides them to the user interface 416 for display to the user.

The digital signal processor 402 preferably executes a set of software instructions stored in ROM 412. Typically, configuration parameters are provided by the software programmer so that some aspects of the digital signal processor's operation can be customized by the user via interface 416 and system controller 414. Preferably, the set of software instructions causes the digital signal processor 402 to perform density measurements according to one or more of the methods detailed further below. The digital signal processor preferably includes digital to analog (D/A) and analog to digital (A/D) conversion circuitry for providing and receiving analog signals to off-chip components. Generally, most on-chip operations by the digital signal processor are performed on digital signals.

In performing one of the methods described further below, the digital signal processor 402 provides a voltage signal to the voltage-to-frequency converter 404. The voltage-to-frequency converter 404 produces a frequency signal having a frequency proportional to the input voltage. The current driver 406 receives this frequency signal and amplifies it to drive the vibration source 110. The vibration source 110 causes the flow tube to vibrate, and the vibrations are detected by vibration detector 112. A filter/amplifier 408 receives the detection signal from vibration detector 112 and provides some filtering and amplification of the detection signal before passing the detection signal to the amplitude detector 410. The filter/amplifier 408 serves to isolate the vibration detector 112 from the amplitude detector 410 to prevent the amplitude detector 410 from electrically loading the vibration detector 112 and thereby adversely affecting the detection sensitivity. The amplitude detector 410 produces a voltage signal indicative of the amplitude of the detection signal. The digital signal processor 402 measures this voltage signal, and is thereby able to determine a vibration amplitude for the chosen vibration frequency.

Figure 5:
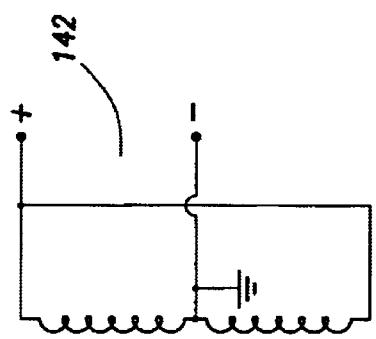
FIG. 5 shows a graph of an exemplary resonance peak.
Figure 5:
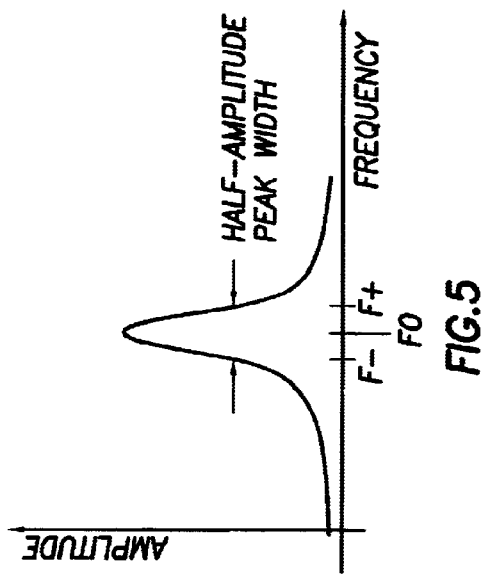

The measurement module employs the vibration source 110 and vibration detector 112 to locate and characterize the resonance frequencies of the flow tube 108. Several different methods are contemplated. In a first method, the measurement module causes the vibration source 110 to perform a frequency "sweep" across the range of interest, and record the amplitude readings from the vibration detector 112 as a function of the frequency. As shown in FIG. 5, a plot of the vibration amplitude versus frequency will show a peak at the resonance frequency $f_0$. The resonance frequency can be converted to a density measurement, and the shape of the peak may yield additional information such as viscosity and multiple phase information.

Figure 6:
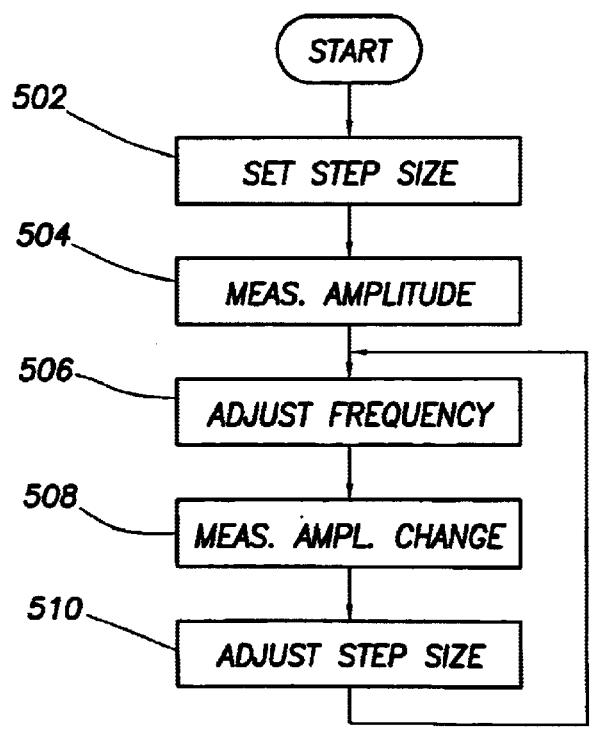
FIG. 6 shows a method for adaptive tracking of a resonance frequency.

In a second method, the measurement module adaptively tracks the resonance frequency using a feedback control technique. One implementation of this method is shown in FIG. 6. An initial step size for changing the frequency is chosen in block 502. This step size can be positive or negative, to respectively increase or decrease the frequency. In block 504, the vibration source is activated and an initial amplitude measurement is made. In block 506, the vibration frequency is adjusted by an amount determined by the step size. In block 508, a measurement of the amplitude at the new frequency is made, and from this, an estimate of the derivative can be made. The derivative may be estimated to be the change in amplitude divided by the change in frequency, but the estimate preferably includes some filtering to reduce the effect of measurement noise. From this estimated derivative, a distance and direction to the resonance peak can be estimated. For example, if the derivative is large and positive, then referring to FIG. 5 it becomes clear that the current frequency is less than the resonance frequency, but the resonance frequency is nearby. For small derivatives, if the sign of the derivative is changing regularly, then the current frequency is very near the resonance frequency. For small negative derivatives without any changes of sign between iterations, the current frequency is much higher than the resonance frequency. Returning to FIG. 6, this information is used to adjust the step size in block 510, and the digital signal processor 402 returns to block 506. This method may work best for providing a fast measurement response to changing fluid densities.

Figure 8:
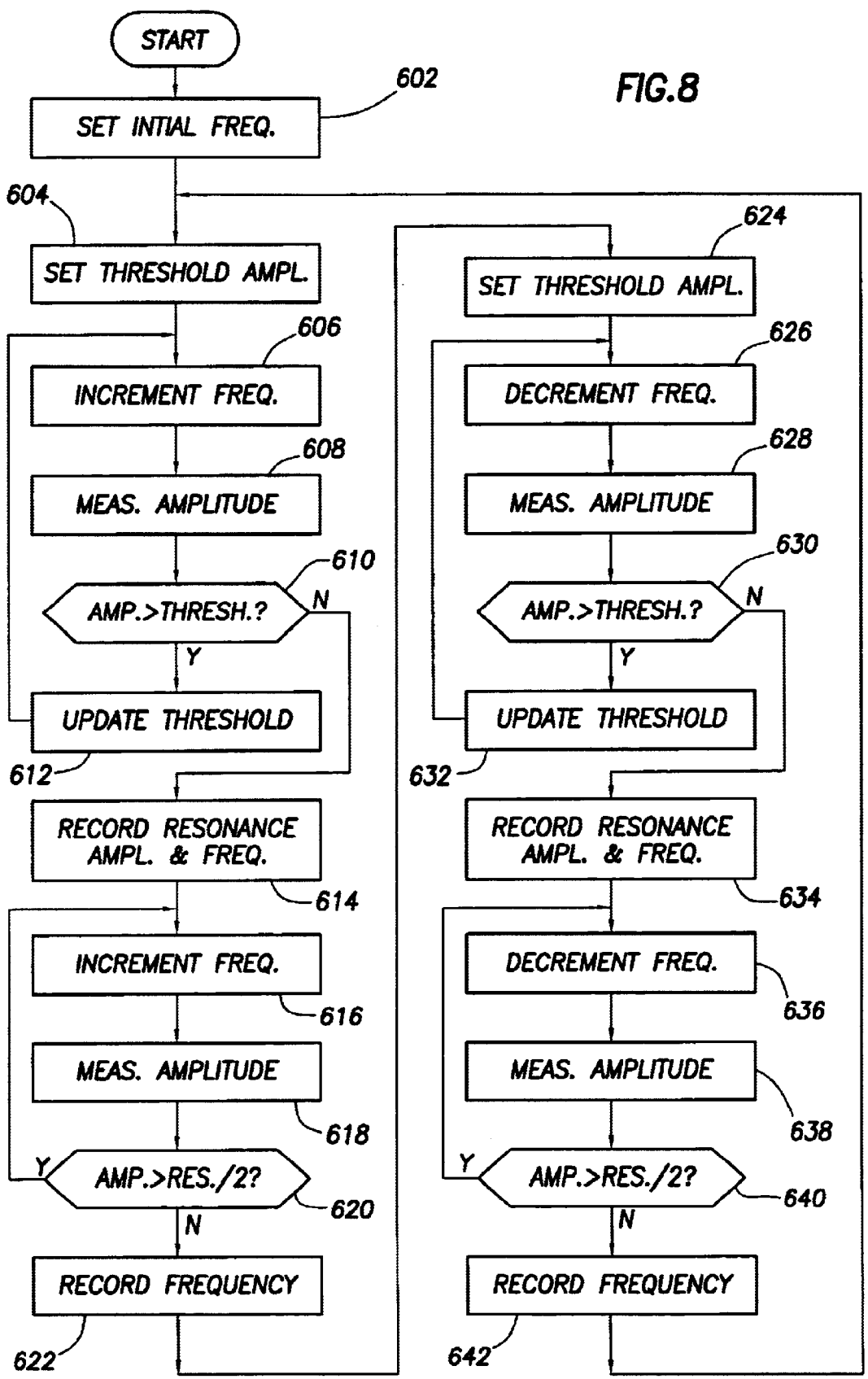
FIG. 8 shows a method for measuring resonance peak frequency, amplitude, and width.

In a third method, the measurement module employs an iterative technique to search for the maximum amplitude as the frequency is discretely varied. Any of the well-known search algorithms for minima or maxima may be used. One illustrative example is now described, but it is recognized that the invention is not limited to the described details. In essence, the exemplary search method uses a back-and-forth search method in which the measurement module sweeps the vibration source frequency from one half-amplitude point across the peak to the other half-amplitude point and back again. One implementation of this method is shown in FIG. 8. In block 602, vibration is induced at an initial (minimum) frequency. In block 604, the vibration amplitude at the current vibration frequency is measured and set as a threshold. In block 606, the frequency is increased by a predetermined amount, and in block 608, the amplitude at the new frequency is measured. Block 610 compares the measured amplitude to the threshold, and if the amplitude is larger, then the threshold is set equal to the measured amplitude in block 612. Blocks 606–612 are repeated until the measured amplitude falls below the threshold. At this point, the threshold indicates the maximum measured amplitude, which occurred at the resonance peak. The amplitude and frequency are recorded in block 614. The frequency increases and amplitude measurements continue in blocks 616 and 618, and block 620 compares the amplitude measurements to half the recorded resonance frequency. Blocks 616–620 are repeated until the amplitude measurement falls below half the resonance peak amplitude, at which point, the half-amplitude frequency is recorded in block 622. Blocks 624–642 duplicate the operations of corresponding blocks 602–622, except that the frequency sweep across the resonance peak occurs in the opposite direction. For each peak crossing, the measurement module records the resonance amplitude and frequency, and then records the subsequent half-amplitude frequency. From this information the peak width and asymmetry can be determined, and the fluid density, viscosity, and multiple phase information can be calculated.

Mathematical Methods

The following notation is used for the resonance frequency derivation:

| | |
|---|---|
| A | vibration system constant (22.4 fixed ends, 22.4 free ends, 3.52 cantilevered on one end) |
| A | calibration coefficient (lbf/in$^3$-sec$^2$) |
| B | calibration coefficient (lbf/in$^3$) |
| $f_n$ | natural frequency (Hz) |
| p | period of natural frequency (sec) |
| $\rho$ | fluid density (lbf/in$^3$) |
| $\rho_t$ | tube material density (lbf/in$^3$) |
| $\mu$ | system mass per unit length (lbf-sec$^2$/in$^2$) |
| $\mu_f$ | fluid mass per unit length (lbf-sec$^2$/in$^2$) |
| $\mu_t$ | tube mass per unit length (lbf-sec$^2$/in$^2$) |
| $d_o$ | tube outside diameter (in) |
| $d_i$ | tube inside diameter (in) |
| l | tube length (in) |
| E | tube modulus of elasticity (psi) |
| I | area moment of inertia of the tube cross section (in$^4$) |
| g | gravitational constant (386.4 in/sec$^2$) |
| q(T) | thermal response of system |
| k(T,P) | pressure response of system |
| T | temperature of system (° C.) |
| P | pressure of fluid in tube (psi) |

The natural frequency of the tube can be calculated as follows (see page 1–14 of the Shock and Vibration Handbook, McGraw Hill, N.Y., 1976.):

$$f_n = \frac{A}{2\pi}\sqrt{\frac{E \cdot I}{\mu \cdot l^4}} \quad \text{(Hz)} \tag{1}$$

A is determined by the geometry of the system, and is 22.4 for the first mode of vibration in a tube with fixed ends or free ends. The area moment of inertia of a tube (I) is given by:

$$I = \frac{\pi d_o^4}{64}\left(1 - \frac{d_i^4}{d_o^4}\right) \quad (\text{in}^4) \tag{2}$$

The mass per unit length $\mu$ consists of the tube's weight and the fluid's weight divided by the length of the tube and the gravitational constant (g=386.4 in/sec2):

$$\mu_t = \frac{\rho_t \pi}{g}\frac{(d_o^2 - d_i^2)}{4} \quad (\text{lbf-sec2/in2}) \tag{3}$$

$$\mu_f = \frac{\rho\pi}{g}\frac{d_i^2}{4} \quad (\text{lbf-sec2/in2}) \tag{4}$$

$$\mu = \mu_t + \mu_f = \frac{\rho_t d_o^2 \pi}{g4}\left(1 - \frac{d_i^2}{d_o^2}\left(1 - \frac{\rho}{\rho_t}\right)\right) \quad (\text{lbf-sec2/in2}) \tag{5}$$

Substituting Equations 2 and 5 into Equation 1 yields an estimate of the natural frequency:

$$f_n = \frac{A}{2\pi}\sqrt{\frac{E \cdot \frac{\pi d_o^4}{64}\left(1 - \frac{d_i^4}{d_o^4}\right)}{\frac{\rho_t d_o^2 \pi}{g4}\left(1 - \frac{d_i^2}{d_o^2}\left(1 - \frac{\rho}{\rho_t}\right)\right) \cdot l^4}}$$

$$= \frac{A d_o}{8\pi l^2}\sqrt{\frac{\frac{Eg}{\rho_t}\left(1 - \frac{d_i^4}{d_o^4}\right)}{1 - \frac{d_i^2}{d_o^2}\left(1 - \frac{\rho}{\rho_t}\right)}} \quad \text{(Hz)} \tag{6}$$

Solving Equation 6 for density yields:

$$\rho = Eg\left(\frac{Ad_o^2}{f_n 8\pi d_i l^2}\right)^2\left(1 - \frac{d_i^4}{d_o^4}\right) - \rho_t\left(\frac{d_o^2}{d_i^2} - 1\right) \tag{7}$$

Equation 7 can be expressed in terms of coefficients A & B:

$$\rho = A/f_n^2 - B \tag{8}$$

Where the coefficients A & B are determined by the tube's material properties and geometry:

$$A = Eg\left(\frac{Ad_o^2}{8\pi d_i l^2}\right)^2\left(1 - \frac{d_i^4}{d_o^4}\right) \tag{9}$$

$$B = \rho_t\left(\frac{d_o^2}{d_i^2} - 1\right) \tag{10}$$

As can be seen in the above equations, the natural frequency of the system is determined by the density of the fluid contained within the tube and the dimensions of the tube and the modulus of elasticity of the tube material. Assuming that the tube is unconstrained with respect to dimensional changes due to temperature and pressure, these changes may be calculated by applying thermal expansion and thick-walled pipe pressure corrections to the spatial dimensions. Formulas for the dimensional variation of tubular members are described in a variety of texts, the most well known being Roark's Formulas for Stress and Strain.

Also affected by the change in temperature of the system is the elastic modulus (E) of the tube material. In 1958, L. F. Vosteen conducted tests in which the elastic modulus was measured as a function of temperature for a number of materials, including titanium alloys.

Therefore, the dimensional variables, as well as elasticity modulus, expressed in equations 9 and 10 above can be expressed as functions dependent on temperature and the coefficients A and B expressed as follows:

$$A(T, P) = \frac{E(T)g A^2}{64\pi^2} * \left(\frac{d_o^4(T, P)}{d_i^2(T, P) * l^4(T, P)}\right) * \left(1 - \frac{d_i^4(T, P)}{d_o^4(T, P)}\right) \tag{11}$$

$$B(T, P) = \rho_t * \left(1 - \left(\frac{d_o^2(T, P)}{d_i^2(T, P)}\right)\right) \tag{12}$$

In practice, the coefficients A and B can be estimated by fitting a calibration curve. Using two fluids of known density, such as water and air, at identical temperature ($T_{cal}$) and pressure ($P_{cal}$) conditions, values for A and B be calculated using equation 8 and measuring the resonant frequency of the system with the two known fluids. Generalizing equations 11 and 12 for all temperatures and pressures and expressing A and B in view of the calibration parameters yields:

$$A(T, P) = \frac{A(T_{cal}, P_{cal}) * \frac{E(T, P)}{E(T_{cal}, P_{cal})} * \left(\frac{d_o^4(T, P)}{d_i^2(T, P) * l^4(T, P)} * \left(1 - \frac{d_i^4(T, P)}{d_o^4(T, P)}\right)\right)}{\left(\frac{d_o^4(T_{cal}, P_{cal})}{d_i^2(T_{cal}, P_{cal}) * l^4(T_{cal}, P_{cal})} * \left(1 - \frac{d_i^4(T_{cal}, P_{cal})}{d_o^4(T_{cal}, P_{cal})}\right)\right)} \tag{13}$$

$$B(T, P) = B(T_{cal}, P_{cal}) * \frac{l(T_{cal}, P_{cal}) * (r_o^2(T_{cal}, P_{cal}) - r_i^2(T_{cal}, P_{cal0}))}{l(T, P) * (r_o^2(T, P) - r_i^2(T, P))} * \frac{\left(1 - \left(\frac{d_o^2(T, P)}{d_i^2(T, P)}\right)\right)}{\left(1 - \left(\frac{d_o^2(T_{cal}, P_{cal})}{d_i^2(T_{cal}, P_{cal})}\right)\right)} \tag{14}$$

The thermal dependence (q(T)) and pressure dependence (k(T,P)) of the system are also determined empirically and realized as a linear functions of the temperature and pressure of the system. A semi-empirical model of the system allowing calculation of the frequency as a function of temperature, pressure, and density.

$$f_n = \left(\sqrt{\frac{A(T, P)}{\rho - B(T, P)}}\right) * q(T) * k(T, P) \quad (15)$$

Using this model, one may determine the fluid density by measuring the resonant frequency at any known temperature and pressure:

$$\rho_f = \left(\frac{A(T, P) * q^2(T) * k^2(T, P)}{f^2}\right) + B(T, P) \quad (16)$$

Using the equations described above, and a densitometer constructed in accordance with the present invention, an unknown fluid can be characterized. The first step is to determine the resonant frequency of the system with a sample of a fluid of known density at a controlled temperature and pressure. The second step is to determine the resonant frequency of the system with a sample of a second fluid of known density at a the same controlled temperature and pressure. Using these two determined resonant frequencies the calibration coefficients A and B can be determined. Once the calibration coefficients are calculated, the sample cavity can be filled with and unknown fluid at a known temperature and pressure. The resonant frequency of the sample cavity can then be determined and the density of the fluid calculated.

Applications

Figure 7:
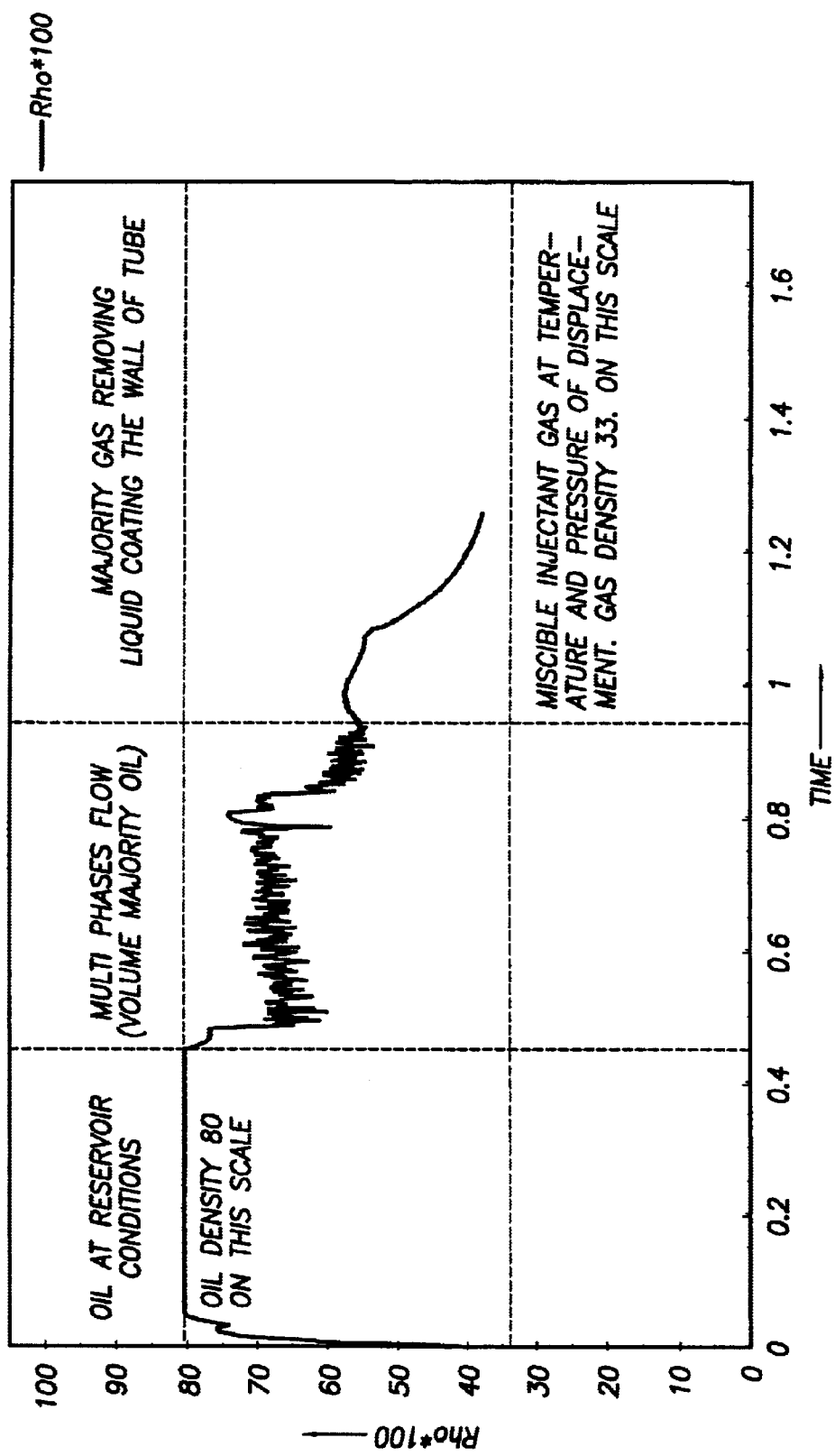
FIG. 7 shows a graph of a measured density as a function of time.

FIG. 7 shows an example of density measurements made according to the disclosed method as a function of time. Initially, the sample flow tube fills with oil, and the density measurement quickly converges to a specific gravity of 0.80. As a miscible gas is injected into the flow stream, the sample tube receives a multiple-phase flow stream, and the density measurement exhibits a significant measurement variation. As the flow stream becomes mostly gas, the oil forms a gradually thinning coating on the wall of the tube, and the density measurement converges smoothly to 0.33. It is noted, that in the multiple-phase flow region, the density measurement exhibits a variance that may be used to detect the presence of multiple phases.

Air or gas present in the flowing fluid affects the densitometer measurements. Gas that is well-mixed or entrained in the liquid may simply require slightly more drive power to keep the tube vibrating. Gas that breaks out, forming voids in the liquid, will reduce the amplitude of the vibrations due to damping of the vibrating tube. Small void fractions will cause variations in signals due to local variation in the system density, and power dissipation in the fluid. The result is a variable signal whose envelope corresponds to the densities of the individual phases. In energy-limited systems, larger void fractions can cause the tube to stop vibrating altogether when the energy absorbed by the fluid exceeds that available. Nonetheless, slug flow conditions can be detected by the flowmeter electronics in many cases, because they manifest themselves as periodic changes in measurement characteristics such as drive power, measured density, or amplitude. Because of the ability to detect bubbles, the disclosed densitometer can be used to determine the bubble-point pressure. As the pressure on the sample fluid is varied, bubbles will form at the bubble point pressure and will be detected by the disclosed device.

If a sample is flowing through the tube continuously during a downhole sampling event, the fluids will change from borehole mud, to mud filtrate and cake fragments, to majority filtrate, and then to reservoir fluids (gas, oil or water). When distinct multiple phases flow through the tube, the sensor output will oscillate within a range bounded by the individual phase densities. If the system is finely homogenized, the reported density will approach the bulk density of the fluid. To enhance the detection of bulk fluid densities, the disclosed measurement devices may be configured to use higher flow rates through the tube to achieve a more statistically significant sample density. Thus, the flow rate of the sample through the device can be regulated to enhance detection of multiple phases (by decreasing the flow rate) or to enhance bulk density determinations (by increasing the flow rate). If the flow conditions are manipulated to allow phase settling and agglomeration (intermittent flow or slipstream flow with low flow rates), then the vibrating tube system can be configured to accurately detect multiple phases at various pressures and temperatures. The fluid sample may be held stagnant in the sample chamber or may be flowed through the sample chamber.

Peak shapes in the frequency spectrum may provide signatures that allow the detection of gas bubbles, oil/water mixtures, and mud filtrate particles. These signatures may be identified using neural network "template matching" techniques, or parametric curve fitting may be preferred. Using these techniques, it may be possible to determine a water fraction from these peak shapes. The peak shapes may also yield other fluid properties such as compressibility and viscosity. The power required to sustain vibration may also serve as an indicator of certain fluid properties.

In addition, the resonance frequency (or frequency difference) may be combined with the measured amplitude of the vibration signal to calculate the sample fluid viscosity. The density and a second fluid property (e.g. the viscosity) may also be calculated from the resonance frequency and one or both of the half-amplitude frequencies. Finally, vibration frequency of the sample tube can be varied to determine the peak shape of the sample tube's frequency response, and the peak shape used to determine sample fluid properties.

The disclosed instrument can be configured to detect fluid types (e.g. fluids may be characterized by density), multiple phases, phase changes and additional fluid properties such as viscosity and compressibility. The tube can be configured to be highly sensitive to changes in sample density and phases. For example, the flow tubes may be formed into any of a variety of bent configurations that provide greater displacements and frequency sensitivities. Other excitation sources may be used. Rather than using a variable frequency vibration source, the tubes may be knocked or jarred to cause a vibration. The frequencies and envelope of the decaying vibration will yield similar fluid information and may provide additional information relative to the currently preferred variable frequency vibration source.

The disclosed devices can quickly and accurately provide measurements of downhole density and pressure gradients. The gradient information is expected to be valuable in determining reservoir conditions at locations away from the immediate vicinity of the borehole. In particular, the gradient information may provide identification of fluids contained in the reservoir and the location(s) of fluid contacts. Table 2 shows exemplary gradients that result from reservoir fluids in a formation.

Determination fluid contacts(Gas/Oil and Oil/Water) is of primary importance in reservoir engineering. A continuous vertical column may contain zones of gas, oil and water. Current methods require repeated sampling of reservoir pressures as a function of true vertical depth in order to calculate the pressure gradient (usually psi/ft) in each zone. A fluid contact is indicated by the intersection of gradients from two adjacent zones (as a function of depth). Traditionally, two or more samples within a zone are required to define the pressure gradient.

The pressure gradient ($\Delta p/\Delta h$) is related to the density of the fluid in a particular zone. This follows from the expression for the pressure exerted by a hydrostatic column of height h.

$$P = \rho * g * h \qquad (17)$$

TABLE 2

| Fluid | Density Gm/cc | Gradient psi/ft |
|---|---|---|
| Low Pressure Gas Cap | 0.10 | 0.04 |
| Gas Condensate | 0.20 | 0.09 |
| Light Oil | 0.50 | 0.22 |
| Med. Oil | 0.70 | 0.30 |
| Heavy Oil | 0.90 | 0.39 |
| Pure Water | 1.00 | 0.43 |
| Formation Water | ≧1.00 | ≧0.43 |
| Mud Filtrate (from 8.7 ppg) | 1.04 | 0.45 |
| Completion Brine | 1.08 | 0.47 |
| Mud (12.5 ppg) | 1.50 | 0.65 | where P denotes pressure, $\rho$ denotes density, g denotes gravitational acceleration, and h denotes elevation.

In a particular zone, with overburden pressure which differs from that of a continuous fluid column, the density of the fluid may be determined by measuring the pressure at two or more depths in the zone, and calculating the pressure gradient:

$$\rho = \frac{\Delta P / \Delta h}{g} \qquad (18)$$

However, the downhole densitometer directly determines the density of the fluid. This allows contact estimation with only one sample point per zone. If multiple samples are acquired within a zone, the data quality is improved. The gradient determination can then be cross-checked for errors which may occur. A high degree of confidence is achieved when both the densitometer and the classically determined gradient agree.

Once the gradient for each fluid zone has been determined, the gradient intersections of adjacent zones are determined. The contact depth is calculated as the gradient intersection at true vertical depth.

Numerous variations and modifications will become apparent to those skilled in the art once the above disclosure is fully appreciated. For example, the flow tubes may be replaced with sample chambers of any rigid variety. It is intended that the following claims be interpreted to embrace all such variations and modifications.

What is claimed is:

1. A method for using a vibratory resonant densitometer to characterize a fluid, the method comprising:
   calibrating the densitometer by determining the vibratory resonant frequency of a tubular sample cavity with each of two fluids at single controlled temperature and pressure; wherein each fluid has a different known density;
   receiving a sample fluid of an unknown density into the tubular sample cavity at a known temperature and pressure;
   determining a vibratory resonant frequency of the tubular sample cavity;
   calculating the unknown fluid density using the vibratory resonant frequency and compensating for the known temperature and pressure conditions of the sample fluid versus the controlled temperature and pressure conditions at which the tubular sample cavity was calibrated; wherein the compensating is dependent on the geometry and composition of the sample cavity.

2. A method for using a vibratory resonant densitometer to characterize a fluid, the method comprising:
   receiving a sample fluid into a sample cavity constructed of a sample cavity material;
   determining a resonant frequency of the sample cavity;
   calculating a fluid density using the resonant frequency and compensating for actual conditions of the sample fluid versus conditions at which the sample cavity was calibrated; wherein the fluid density ($\rho$) is determined in accordance with the equation:

$$\rho = A/f_n^2 - B$$

wherein A and B are coefficients determined by geometry and composition of the sample cavity, and wherein $f_n$ is the natural frequency of the sample cavity.

3. The method of claim 2 where the coefficients A and B correspond to:

$$A = Eg\left(\frac{Ad_o^2}{8\pi d_i l^2}\right)^2 \left(1 - \frac{d_i^4}{d_o^4}\right); \text{ and}$$

$$B = \rho_t\left(\frac{d_o^2}{d_i^2} - 1\right);$$

where E is a modulus of elasticity of the sample cavity material; g is a gravitational constant; $d_o$ is an outside diameter of the sample cavity, A is a vibration constant, $d_i$ is an inner diameter of the sample cavity; l is a length of the sample cavity; and $\rho_t$ is a density of the sample cavity material.

4. A method for using a vibratory resonant densitometer to characterize a fluid, the method comprising:
   receiving a sample fluid into a sample cavity constructed of a sample cavity material;
   determining a resonant frequency of the sample cavity;
   calculating a fluid density using the resonant frequency and compensating for actual conditions of the sample fluid versus conditions at which the sample cavity was calibrated; wherein the fluid density ($\rho_f$) is determined in accordance with the equation:

$$\rho_f = \left(\frac{A(T, P) * q^2(T) * k^2(T, P)}{f^2}\right) + B(T, P);$$

wherein T is temperature, P is pressure, A and B are coefficients determined by geometry and composition of the sample cavity, q is a thermal dependence of the sample cavity, k is a pressure dependence of the sample cavity, and f is the resonant frequency of the sample cavity.

5. The method of claim 4 where the coefficients A and B are represented by:

$$A = Eg\left(\frac{Ad_o^2}{8\pi d_i l^2}\right)^2\left(1 - \frac{d_i^4}{d_o^4}\right); \text{ and}$$

$$B = \rho_t\left(\frac{d_o^2}{d_i^2} - 1\right);$$

where E is a modulus of elasticity of the sample cavity material; g is a gravitational constant; $d_o$ is an outside diameter of the sample cavity, A is a vibration constant, $d_i$ is an inner diameter of the sample cavity; l is a length of the sample cavity; and $\rho_t$ is a density of the sample cavity material.

6. The method of claim 5 wherein coefficients A an B vary as a function of temperature and pressure.

7. The method of claim 6 wherein the values of A and B at sample temperature and pressure are determined using values of A and B determined at calibration temperature and pressure.

* * * * *